US011053546B2

(12) United States Patent
Del Favero et al.

(10) Patent No.: US 11,053,546 B2
(45) Date of Patent: Jul. 6, 2021

(54) METHOD AND SYSTEM FOR ESTIMATING WHETHER A FEMALE IS PREGNANT BASED ON A BLOOD SAMPLE

(71) Applicant: AGILENT TECHNOLOGIES, INC., Santa Clara, CA (US)

(72) Inventors: Jurgen Peter Lode Del Favero, Niel (BE); Michaël Vyverman, Niel (BE); Paul Vauterin, Niel (BE)

(73) Assignee: AGILENT TECHNOLOGIES, INC., Santa Clara, CA (US)

( * ) Notice: Subject to any disclaimer, the term of this patent is extended or adjusted under 35 U.S.C. 154(b) by 298 days.

(21) Appl. No.: 15/737,105

(22) PCT Filed: Jul. 13, 2016

(86) PCT No.: PCT/EP2016/066654
§ 371 (c)(1),
(2) Date: Dec. 15, 2017

(87) PCT Pub. No.: WO2017/063769
PCT Pub. Date: Apr. 20, 2017

(65) Prior Publication Data
US 2018/0171404 A1 Jun. 21, 2018

(30) Foreign Application Priority Data

Oct. 14, 2015 (BE) .................................. 2015/5658

(51) Int. Cl.
*G16B 20/00* (2019.01)
*G16H 50/20* (2018.01)
(Continued)

(52) U.S. Cl.
CPC ......... *C12Q 1/6881* (2013.01); *C12Q 1/6827* (2013.01); *G01N 33/49* (2013.01);
(Continued)

(58) Field of Classification Search
None
See application file for complete search history.

(56) References Cited

U.S. PATENT DOCUMENTS

2006/0252068 A1 11/2006 Lo et al.

FOREIGN PATENT DOCUMENTS

IL 201759 A 4/2013
KR 20150032062 A 3/2015
(Continued)

OTHER PUBLICATIONS

Fan, H.C. et al. Nature 487:320 (Jul. 19, 2012). (Year: 2012).*
Illanes et al., "Early detection of cell-free fetal DNA in maternal plasma" Early Human Development, vol. 83, 2007, pp. 563-566.
(Continued)

*Primary Examiner* — Diana B Johannsen
(74) *Attorney, Agent, or Firm* — Arent Fox LLP

(57) ABSTRACT

A method for estimating whether a female is pregnant, said method comprising measuring allele presences (D) for a plurality of genetic markers of at least one chromosome, different from the X and Y chromosome, in a sample of cell-free DNA from a potentially pregnant female; each allele presence representing the presence at a genetic marker of at least one of: a reference allele of maternal or foetal origin, and an alternative allele of maternal or foetal origin; based on said measured allele presences, determining a homozygous fraction ($F_{ho}$) thereof which is associated with purely homozygous genetic markers; and estimating whether the female is pregnant based on said fraction.

10 Claims, 5 Drawing Sheets

(51) Int. Cl.
*C12Q 1/6881* (2018.01)
*C12Q 1/6827* (2018.01)
*G16H 10/40* (2018.01)
*G01N 33/49* (2006.01)
*G01N 33/68* (2006.01)

(52) U.S. Cl.
CPC .......... G01N 33/689 (2013.01); G16B 20/00 (2019.02); G16H 10/40 (2018.01); G16H 50/20 (2018.01); *C12Q 2535/122* (2013.01); *C12Q 2537/165* (2013.01); *C12Q 2600/156* (2013.01); *C12Q 2600/172* (2013.01)

(56) References Cited

FOREIGN PATENT DOCUMENTS

| | | |
|---|---|---|
| WO | WO 2012/142334 A2 | 10/2012 |
| WO | WO 2014/209597 A2 | 12/2014 |

OTHER PUBLICATIONS

International Search Report issued in international patent application No. PCT/EP2016/066654, dated Sep. 27, 2016 (4 pages).
Lo et al., "Genomic Analysis of Fetal Nucleic Acids in Maternal Blood," Annual Review of Genomics and Human Genetics, Sep. 2012, vol. 13(1), pp. 285-306.
Tynan et al., "Restriction Enzyme-Mediated Enhanced Detection of Circulating Cell-Free Fetal DNA in Maternal Plasma," The Journal of Molecular Diagnostics, vol. 13(4), Jul. 2011, pp. 382-389.

\* cited by examiner

METHOD AND SYSTEM FOR ESTIMATING WHETHER A FEMALE IS PREGNANT BASED ON A BLOOD SAMPLE

CROSS REFERENCE TO RELATED APPLICATIONS

This application is a 35 U.S.C. 371 National Phase of PCT Application No. PCT/EP2016/066654 filed Jul. 13, 2016, which claims benefit to BE Application No. 2015/5658 filed Oct. 14, 2015, the disclosure of which is hereby incorporated by reference in its entirety.

FIELD OF INVENTION

The field of the invention relates to estimating whether or not a female is pregnant based on a blood sample. Particular embodiments of the inventions relate to methods, systems, computer programs and computer program products for estimating whether or not a female is pregnant.

BACKGROUND

WO 2013/057568 in the name of the Applicant discloses prenatal detection methods using non-invasive techniques. In particular, it relates to prenatal diagnosis of a foetal chromosomal aneuploidy by detecting foetal and maternal nucleic acids in a maternal biological sample. More particularly, WO 2013/057568 applies multiplex PCR to amplify selected fractions of the respective chromosomes of maternal and foetal chromosomes. Respective amounts of suspected aneuploid chromosomal regions and chromosomes are determined from massive sequencing analysis followed by a statistical analysis to detect a particular aneuploidy.

Although various prenatal detection methods exist, there is a need for an improved method to estimate whether or not a female is pregnant in case only a blood sample of that female is provided.

SUMMARY

The object of embodiments of the invention is to provide a method, system and computer program for estimating whether or not a female is pregnant based on a blood sample.

According to a first aspect of the invention there is provided a method for estimating whether a female is pregnant. The method comprises measuring allele presences (D) for a plurality of genetic markers of at least one chromosome, different from the X and Y chromosome, in a sample of cell-free DNA from a potentially pregnant female. Each allele presence represents the presence at a genetic marker of at least one of: a reference allele of maternal or foetal origin, and an alternative allele of maternal or foetal origin. For the sake of completeness, it is noted that this does not imply that a distinction can be made between an allele of maternal origin and an allele of foetal origin, but merely that an allele of either origin may be measured. The method further comprises, based on said measured allele presences, determining a homozygous fraction ($F_{ho}$) thereof which is associated with purely homozygous genetic markers; and estimating whether the female is pregnant based on said fraction. In the event of a sample of a pregnant female, the term "purely homozygous genetic marker" refers to a genetic marker which is both homozygous in the DNA of maternal origin and in the DNA of foetal origin. In the event of a sample of a non-pregnant female, the term "purely homozygous genetic marker" refers simply to a homozygous genetic marker which is homozygous in the DNA of the female.

Embodiments of the invention are based inter alia on the inventive insight that the homozygous fraction is expected to be larger for samples of non-pregnant women than for samples of pregnant women. The reason is that the presence of foetal DNA will move a portion away from the purely homozygous state, because of the presence of foetal DNA based on the father's DNA. This fraction may be determined without actual detection of paternal allele presences.

In the context of this specification, a 'genetic marker' is a position on the genome that is known to take several possible states over individuals in a population.

In an exemplary embodiment the determining of the homozygous fraction comprises: based on said measured allele presences for the plurality of genetic markers, calculating a corresponding number of allele frequencies for said plurality; and determining as the homozygous fraction the fraction of said measured allele presences for which the allele frequency is 0 or 1 within a predetermined error margin. This predetermined error margin may relate to the intrinsic error rate of a sequencing device and may be determined empirically. A person of skill in the art will understand that the error rate of a sequencing device is an industry standard, and will be well known for a specific manufacturer or instrument, but in a specific embodiment the predetermined error margin is <0.02. Particularly it may be <0.015, <0.01 or <0.005. Typically the allele presences are plotted as read counts in function of the allele frequency, and the homozygous fraction corresponds with the read counts of the variant data points concentrated around allele frequency 0 and around allele frequency 1.

In an exemplary embodiment the estimating comprises: estimating that the female is pregnant if the homozygous fraction is below a first predetermined value; and estimating that the female is not pregnant if the homozygous fraction is above a second predetermined value. The first and second predetermined value may be the same. Alternatively the second predetermined value may be larger than the first predetermined value. In a possible embodiment the first threshold and the second threshold is a constant value, optionally the same constant value, which may have been determined empirically. Using the methods as described herein the predetermined values for determining if an individual is may be classified as pregnant are between 0.50-0.75, particularly between 0.55-0.70, more particularly between 0.60-0.68. However, it is understood that other methods and other embodiments may require different threshold values. A person of skill in the art will be able to determine suitable predetermined values for the homozygous fraction for the specific population to be tested, for example from a small test set of individuals whose pregnancy status is known (e.g. using a data set from 5-15 pregnant females and 5-15 non pregnant females, specifically using 10 pregnant and 10 non-pregnant females).

In an exemplary embodiment the method further comprises, based on said measured allele presences, determining a heterozygous fraction ($F_{he}$) thereof which is associated with genetic markers that are heterozygous in the female's DNA. The estimating may then comprise estimating whether the female is pregnant based on the homozygous fraction and said heterozygous fraction. In a further developed embodiment thereof the method comprises calculating a threshold value as a function of the heterozygous fraction. The estimating may then comprise estimating that the female is pregnant if the homozygous fraction is below the calculated threshold value; and estimating that the female is not pregnant if the homozygous fraction is above the calculated threshold value. In that way, the accuracy of the method may be further improved because it may compensate for different levels of overall homozygosity in the female's DNA.

In an exemplary embodiment the determining of a homozygous fraction ($F_{ho}$) which is associated with purely homozygous genetic markers comprises, based on said measured allele presences for the plurality of genetic markers, calculating a corresponding number of allele frequencies for said plurality of genetic markers; and determining read counts in function of the allele frequency for said plurality of genetic markers; selecting a portion of the read counts, preferably a portion in which the read counts with the highest and/or the lowest value(s) are removed; and determining a homozygous fraction ($F_{ho}$) of said selected portion, which is associated with purely homozygous genetic markers. By selecting a portion of the read counts instead of using all read counts the method may be further improved. More in particular, by removing the read counts with the lowest value(s), the accuracy is improved since higher read counts have a more accurate allele frequency because there are more measurement data; and by removing the read counts with the highest value(s), it is avoided that these very high read counts have a disproportionate influence on the fraction determination. In a particular embodiment a person of skill in the art will identify prior to running the experiment the thresholds for removing such "outlier" values taking into consideration the mean and standard deviation of the read count values. In an alternative embodiment the lower threshold for discarding the lowest read count values may be selected based on the specific error rate of the method or sequencing device used. In a particular embodiment the lowest 10% of the read count values are removed, more particularly the lowest 5%, lowest 3%, lowest 1% or lowest 0.5% of the read count values are removed. In a particular embodiment the highest 10% of the read count values are removed, more particularly the highest 5%, highest 3%, highest 1% or highest 0.5% of the read count values are removed.

In an exemplary embodiment the measuring and determining steps are performed for a batch comprising a plurality of samples of the female; wherein for each sample of the batch, the homozygous fraction is calculated; and the estimating is further based on said homozygous fraction of each sample.

According to another aspect of the invention, there is provided a system for estimating whether a female is pregnant. The system comprises a measurement device, a determining module, and an estimating module. The measurement device is configured for measuring allele presences for a plurality of genetic markers of at least one chromosome, different from the X and Y chromosome, in a sample of cell-free DNA from a potentially pregnant female; each allele presence representing the presence at a genetic marker of at least one of: a reference allele of maternal or foetal origin, and an alternative allele of maternal or foetal origin. This may be any commercially available measurement device suitable for performing such measurements. The determining module is configured for determining, based on said measured allele presences, a homozygous fraction thereof which is associated with purely homozygous genetic markers. The estimating module is configured for estimating whether the female is pregnant based on said fraction. In a typical embodiment the determining module and the estimating module are implemented as software.

In an exemplary embodiment the determining module is configured for calculating a corresponding number of allele frequencies for said plurality of genetic markers based on said measured allele presences; and for determining as the homozygous fraction the fraction of said measured allele presences for which the allele frequency is 0 or 1 within a predetermined error margin. A person of skill in the art will understand that the error rate of a sequencing device is an industry standard, and will be well known for a specific manufacturer or instrument, but in a specific embodiment the predetermined error margin is <0.02. Particularly it may be <0.015, <0.01 or <0.005.

In an exemplary embodiment the estimating module is configured for estimating that the female is pregnant if the homozygous fraction is below a first predetermined value; and estimating that the female is not pregnant if the homozygous fraction is above a second predetermined value, wherein the first and second predetermined value may be the same, or wherein the second predetermined value may be larger than the first predetermined value. Using the methods as described herein the predetermined values for determining if an individual is may be classified as pregnant are between 0.50-0.75, particularly between 0.55-0.70, more particularly between 0.60-0.68. However, it is understood that other methods and other embodiments may require different threshold values. A person of skill in the art will be able to determine suitable predetermined values for the homozygous fraction for the specific population to be tested, for example from a small test set of individuals whose pregnancy status is known (e.g. using a data set from 5-15 pregnant females and 5-15 non pregnant females, specifically using 10 pregnant and 10 non-pregnant females).

In an exemplary embodiment the determining module is further configured for, based on said measured allele presences, determining a heterozygous fraction ($F_{he}$) thereof which is associated with heterozygous genetic markers. The estimating module may then be further configured for estimating whether the female is pregnant based on the homozygous fraction and said heterozygous fraction.

In an exemplary embodiment the determining module is further configured for calculating a threshold value as a function of the heterozygous fraction. The estimating module may then be further configured for estimating that the female is pregnant if the homozygous fraction is below the calculated threshold value; and estimating that the female is not pregnant if the homozygous fraction is above the calculated threshold value. The heterozygous fraction is determined as a linear function with a negative slope and a positive intercept. Exemplary methods for determining the heterozygous fraction are described further in the examples, and in FIG. 4. A person of skill in the art is able to use the teaching herein to determine the threshold in function of the heterozygous fraction, using the methods as described or alternatives which are within their common general knowledge.

In an exemplary embodiment the measurement device and determining module are configured to perform the measuring and determining for a batch comprising a plurality of samples, wherein for each sample of the batch, the homozygous fraction is calculated. The estimating module may then be configured for estimating whether the female is pregnant based on said homozygous fraction of each sample.

In a preferred embodiment the estimating module is configured for estimating the pregnancy status of the female in a manner as described in any of the exemplary embodiments of the method.

In a preferred embodiment the measurement device is configured to measure allele presences using at least one of the following: polymerase chain reaction (PCR), ligase chain reaction, nucleic acid sequence based amplification (NASBA), and branched DNA methods; and preferably PCR.

In exemplary embodiments of the invention, the measuring of allele presences may comprise measuring of SNP allele presences and/or measuring allele presences for short insertions and/or deletions.

Preferred embodiments of the method and system of the invention are disclosed in the appended dependent claims.

According to a further aspect of the invention, there is provided a computer program comprising computer-executable instructions to perform, when the program is run on a computer, one or more steps, and in particular the estimating step of embodiments of the method disclosed above. According to a further aspect of the invention, there is provided a computer device or other hardware device programmed to perform one or more steps, and in particular the estimating step of any one of the embodiments of the method disclosed above. According to another aspect there is provided a data storage device encoding a program in machine-readable and machine-executable form to perform one or more steps of any one of the embodiments of the method disclosed above. The reference to computer-executable instructions/form has to be construed such that it comprises both directly executable machine code, code that must be compiled to be executed, and code that is interpreted instead of executed per se.

BRIEF DESCRIPTION OF THE FIGURES

The accompanying drawings are used to illustrate presently preferred non-limiting exemplary embodiments of a method and system of the present invention. The above and other advantages of the features and objects of the invention will become more apparent and the invention will be better understood from the following detailed description when read in conjunction with the accompanying drawings, in which.

DETAILED DESCRIPTION OF EXEMPLARY EMBODIMENTS

Figure 1:
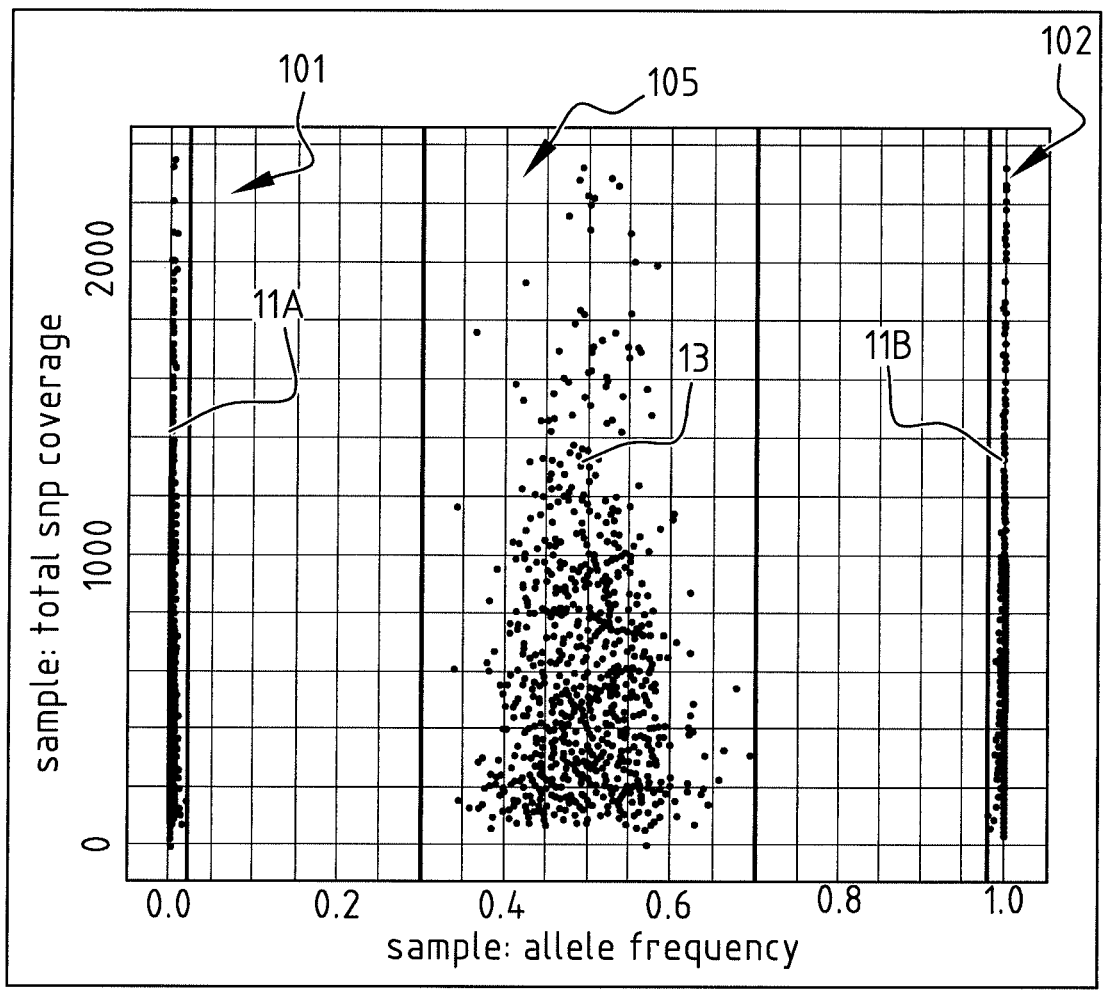
FIG. 1 is a scatterplot showing the total SNP coverage (y-axis) versus allele frequency (x-axis) for a non-pregnant sample NP.

In a Non-Invasive Prenatal Test (NIPT), known in the prior art, cell free DNA (cfDNA) in a maternal serum or plasma sample of a pregnant female is sequenced in order to screen for the presence of chromosomal aneuploidies in the foetus, such as trisomy of chromosome 21. According to exemplary embodiments of the invention, there is provided a method to estimate the whether or not a female is pregnant.

In a typical embodiment, a maternal serum or plasma sample is derived from the maternal blood. This may be a small amount of serum or plasma, e.g. 1 to 20 ml. Depending on the desired accuracy it may be preferred to use larger volumes. The preparation of the serum or plasma from the maternal blood sample may be carried out using standard techniques. Suitable techniques include centrifugation and/or matrix based techniques. In possible embodiments, a sequence-based enrichment method may be used on the maternal serum or plasma to specifically enrich for foetal nucleic acid sequences.

Embodiments of the method of the invention may be carried out for a sample containing foetal DNA at a foetal fraction concentration of the total amount of DNA above a predetermined threshold. In preferred embodiments, an amplification of the foetal DNA sequences in the sample is carried out. Any amplification method known to the skilled person may be used, such as a PCR method.

In a preferred embodiment only data from Applicant's Clarigo test that does not involve the detection of SNP (or single-nucleotide polymorphism, i.e. a genetic marker that comprises a single variable nucleotide) alleles on the foetal DNA that are not present in the DNA of the pregnant female, is used. The Clarigo test consists in targeted sequencing of a number of regions on the human genome (in other words, targeting specific genetic markers), using known SNPs (single-nucleotide polymorphism) with high (e.g. greater than 1%, preferably greater than 10%) population prevalence and two possible alleles (sc. a reference allele a.k.a. REF; and an alternative allele a.k.a. ALT). More details about the Clarigo test can be found on the Internet on at multiplicom.com/product/clarigo, and in WO 2013/057568, which was filed in the name of the Applicant.

Now an exemplary embodiment of a method for estimating whether a female is pregnant will be discussed in detail. In a first measurement step, allele presences for a plurality ($D_R$) of genetic markers of at least one chromosome, different from the X and Y chromosome, are measured in a sample of cell-free DNA from a female. Each allele presence represents the presence at a genetic marker of at least one of: a reference allele of maternal or foetal origin, and an alternative allele of maternal or foetal origin. In a second calculating step, based on said measured allele presences for said plurality, a homozygous fraction ($F_{ho}$) thereof, which is associated with purely homozygous genetic markers, is determined. In a third step it is estimated based on said homozygous fraction whether the female is pregnant.

Measurement and Fraction Determining

An advantageous way to represent the results of measuring allele presences for a genetic marker, is to associate the following information to a variant data point for that genetic marker. A variant data point (being a data point associated with a number of variants, such as alleles) is used in this specification as a convenient representation for a genetic marker, and thus represents the result of measuring allele presences in a number of amplicons for genetic markers. An amplicon is a piece of DNA or RNA that is the (source and/or) product of amplification or replication events. In other words, an amplicon is a biophysical piece of replication material, designed to contain a known SNP position with high population prevalence. Each variant data point is thus associated with a known SNP with high population prevalence and with two possible alleles (sc. a reference allele a.k.a. REF; and an alternative allele a.k.a. ALT). For each variant data point $A_i$ the following numbers can be determined using e.g. a standard bioinformatics pipeline applied on the sequencing data:

The number of reads containing the REF allele on the known SNP position, $C_{Ri}$.

The number of reads containing the ALT allele on the known SNP position, $C_{Ai}$.

The total coverage $C_{Ti} = C_{Ri} + C_{Ai}$.

The allele frequency, or the fraction of ALT allele reads on the total coverage $F_i = C_{Ai}/(C_{Ri} + C_{Ai})$.

Therefore, for a given genetic marker i, the allele presences can be measured for both the REF allele, for the ALT allele, and for both alleles, by measuring the numbers of reads containing the REF allele, the ALT allele and both the REF and the ALT alleles respectively. Based on the measured allele presences, a corresponding number of allele frequencies are calculated for the predetermined number of genetic markers.

For each position in the genome (i.e. for each genetic locus), excluding the X and Y chromosomes and assuming that there are no relevant chromosome disorders, in case of a pregnant female sample, there are four copies present in the sample (assuming the position is not part of an aneuploidy region), which determine the total number of reads: two copies from the maternal DNA and two copies from the foetal DNA.

For an individual variant data point (i.e. for an individual genetic marker), let A and B denote the REF and ALT allele for the known SNP on the maternal DNA for that genetic marker, and a and b the corresponding states for the foetal DNA of a pregnant female. For a non-pregnant sample, the variant data point can be in the possible states AA, AB, BB with, for each of these states, respective expected fraction ALT allele reads ($F_i$) 0, 0.5 and 1. For a pregnant sample the variant data point can be in the possible states listed in Table 1:

TABLE 1

| variant data point state | Expected fraction ALT reads ($F_i$) |
| --- | --- |
| AAaa | 0 |
| AAab | FF/2 |
| ABaa | 0.5 − FF/2 ← (1 − FF)/2 |
| ABab | 0.5 |
| ABbb | 0.5 + FF/2 ← (1 − FF)/2 + FF |
| BBab | 1 − FF/2 |
| BBbb | 1 |

Figure 2:
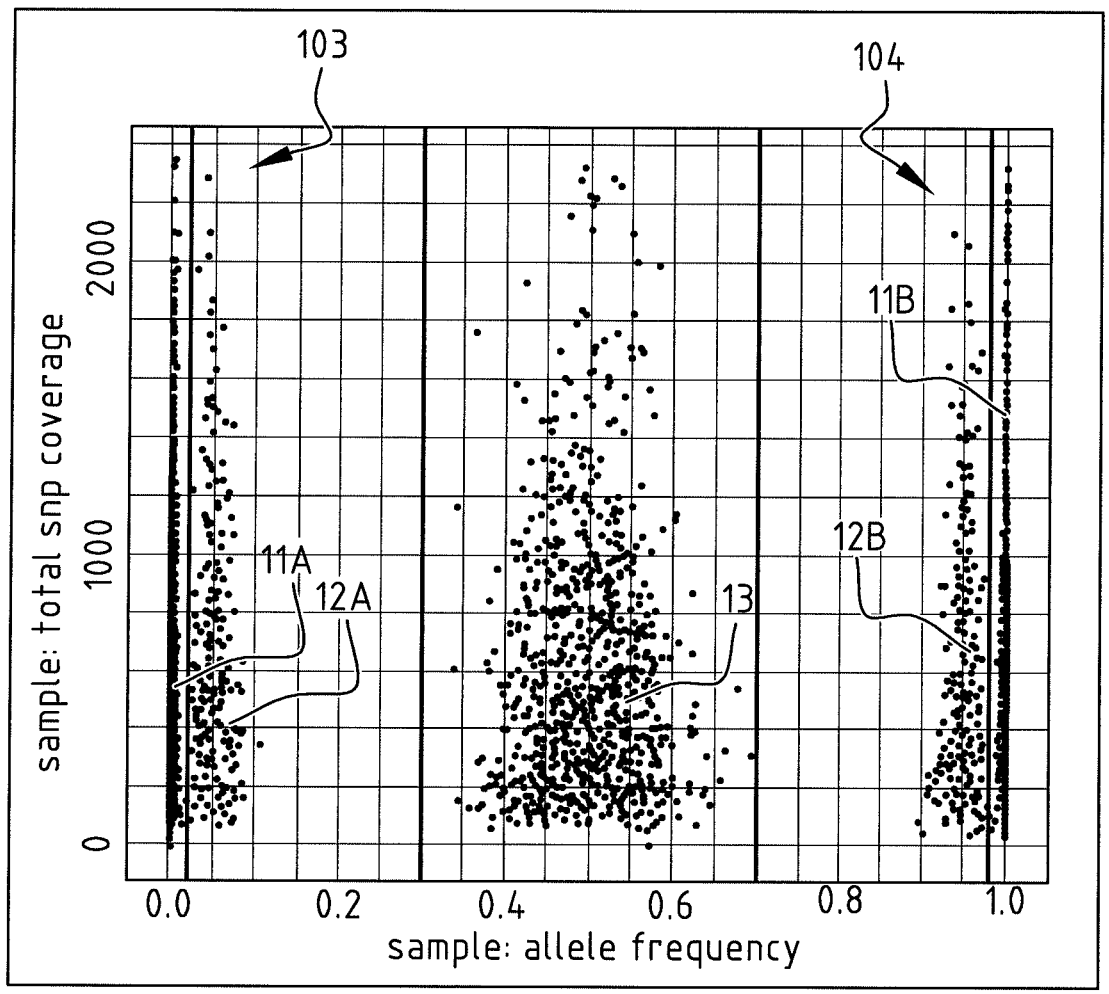
FIG. 2 is a scatterplot showing the total SNP coverage (y-axis) versus allele frequency (x-axis) for a pregnant sample P.

As an illustration of measured allele presences, the scatterplots illustrated in FIGS. 1 and 2 show data for a sample NP (non-pregnant female) and a sample P (pregnant female) for which allele presences for genetic markers for at least one chromosome, being different from the X-chromosome and the Y-chromosome, have been measured, wherein:

Each point is a variant data point (representing the result of measurements made on amplicons) for genetic markers of the at least one chromosome, being different from the X-chromosome and the Y-chromosome.

The horizontal axis shows the fraction of reads with the ALT SNP allele (i.e., the allele frequency F).

The vertical axis shows the total read coverage $C_{Ti}$.

It can be seen from FIG. 1 that specific variant data points are associated with a specific allele frequency. For example, variant data point 101 is shown on the left, and represents a genetic marker for which approximately 2300 reads were performed. All or nearly all reads for this genetic marker have measured the allele presence to indicate that REF alleles (i.e. A) are present, but not that ALT alleles are present (i.e. B). Therefore, variant data point 101 has been plotted on the left in FIG. 1, where the allele frequency is approximately 0, and likely represents a homozygous genetic marker AA. Variant data point 102 is shown on the right, and represents a genetic marker for which approximately 2300 reads were performed. All or nearly all reads for this genetic marker have measured the allele presence to indicate that REF alleles (i.e. A) are not present, but that ALT alleles (i.e. B) are present. Therefore, variant data point 102 has been plotted on the right in FIG. 1, where the allele frequency is approximately 1, and likely represents a homozygous genetic marker BB.

In FIG. 2 variant data point 103 represents a genetic marker for which approximately 2300 reads were performed. The measured allele presences allow one to calculate the allele frequency, which is relatively low, but non-zero. Therefore, variant data point 103 likely represents a genetic marker that is maternally homozygous for the reference allele pair but has a heterozygous allele pair of foetal origin (thus AAab), since the fraction of maternal DNA present in the sample for the genetic marker is (much) greater than the fraction of foetal DNA present in the sample for the genetic marker. Variant data point 104 is shown on the right, and represents a genetic marker for which approximately 2100 reads were performed. By the same reasoning, variant data point 104 likely represents a genetic marker that is maternally homozygous for the alternative allele pair but has a heterozygous allele pair of foetal origin (thus BBab). Note that the remark that 103 and 104 likely represent a marker that is homozygous in the maternal DNA and heterozygous in the foetal DNA is only made to assist the understanding of the figures. Exemplary embodiments of the invention do not rely on such an assessment, as genetic markers represented by 103 and 104 are only labelled as non-homozygous.

In FIG. 1 variant data point 105 represents a genetic marker for which approximately 2300 reads were performed. The measured allele presences allow one to calculate the allele frequency, which is found to be approximately 0.5. Therefore, variant data point 105 likely represents a genetic marker that is heterozygous (thus AB).

Therefore, in FIG. 2, three groups of variant data points (11A and 11B, 12A and 12B, and 13) can be distinguished:

variant data points 11A and 11B that are homozygous in the maternal and foetal DNA (AAaa, BBbb);

variant data points 12A and 12B that are homozygous in the maternal DNA, and heterozygous in the foetal DNA (AAab, BBab). Note that in these cases the foetal DNA contains an allele that was inherited from the father and that is not present in the maternal DNA. In other words, for a male foetus this group of variant data points will not be present for the X-chromosome, see FIG. 1;

variant data points 13 that are heterozygous in the maternal DNA (ABaa, ABab, ABbb). Again, note that this classification is made only to assist the understanding of an exemplary embodiment of the method of the invention, and that the exemplary embodiment does not rely on this exact distinction.

It is noted that multiple variant data points may have the same (or very nearly the same) allele frequency, especially when they are part of the same group. This means that (very nearly) the same number of allele presences has been measured for them, relatively to the total number of reads.

It is also noted that, in FIGS. 1 and 2, variant data points with a higher total read coverage (closer to the top of the plot) generally have a more accurate allele frequency, simply since there are more measurement data. This property may be taken into account when determining a statistical reliability for a given variant data point. More in particular, in an exemplary embodiment, the accuracy of the method may be improved by restricting the set of amplicons based on the total coverage $C_{Ti}$. This may include requiring a minimal total coverage and/or a maximum total coverage, removing a fraction of the total number of amplicons with the highest and/or the lowest total coverage. The reason is that amplicons with a higher total coverage have a more accurate allele frequency, because there are more measurement data. However, amplicons with a total coverage that is much higher than that of the average in the set have a disproportionate influence on the determination of the homozygous fraction.

The following parameters are calculated from the obtained measurement results:

the total number D of reads over all variant data points on the at least one chromosome (this may be all chromosomes excluding the X-chromosome and the Y-chromosome); i.e. the total number of measured allele presences for the plurality of genetic markers of the at least one chromosome;

the total number $D_{ho}$ of reads on the at least one chromosome, corresponding to variant data points that are purely homozygous, i.e. an allele frequency which is either 0 or 1, within a predetermined error margin.

For sample NP, the following set of values is obtained by the method (see FIG. 1 for the variant data points):

D=2000000 (divided among 4000 amplicons), $D_{ho}$=1400000 (divided among a subset of 2900 homozygous amplicons).

For sample P, the following set of values are identified by the method (see FIG. 2 for the variant data points):

D=2000000 (divided among 4000 amplicons), $D_{ho}$=1100000 (divided among a subset of 2200 purely homozygous amplicons).

In the exemplary embodiment, for identifying the set of purely homozygous amplicons for both samples P and NP, allele frequency boundaries of 0.01 and 0.99, have been used.

Next, a homozygous fraction $F_{ho}$ of reads for the plurality of genetic markers, which is associated with purely homozygous genetic markers is calculated:

$$F_{ho}=D_{ho}/D.$$

For sample NP the homozygous fraction $F_{ho}$=0.70 and for sample P $F_{ho}$=0.55. It is clear that the homozygous fraction $F_{ho}$ is higher for sample NP than for sample P.

The value $F_{ho}$ is expected to be larger for samples of non-pregnant women than for samples of pregnant women. The reason is that the presence of foetal DNA will move a fraction of amplicons away from the purely homozygous state, because of the presence of an SNP introduced by the father's DNA. This deviation is measured without actual detection of paternal SNPs.

Estimating

To automate the estimating of whether or not a female is pregnant, there may be established an empirical threshold value $F_T$, distinguishing between non-pregnant and pregnant condition, by optimizing the discrimination using reference data with a known pregnancy condition.

Figure 3:
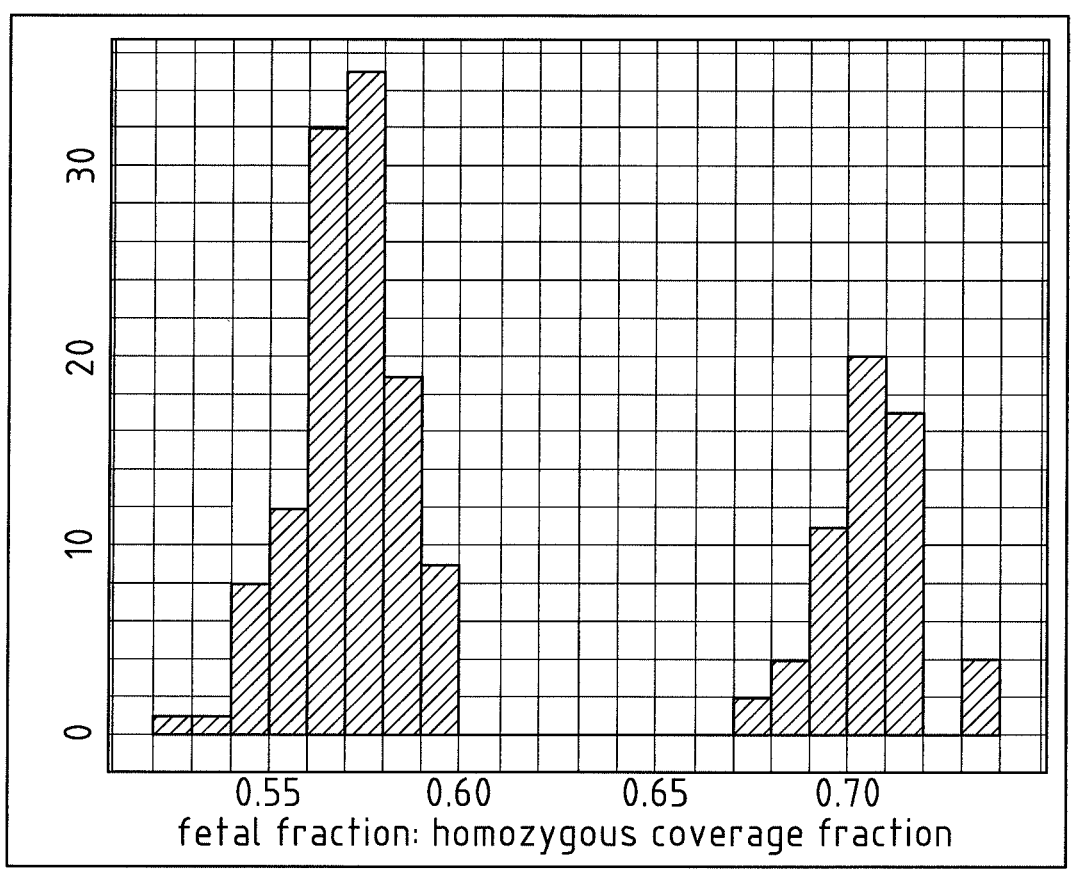
FIG. 3 is a histogram of homozygous fractions of a set of pregnant and non-pregnant female samples.

In an exemplary embodiment, the calculations above are repeated for samples with a given known pregnancy state to establish a threshold value $F_T$. In FIG. 3 a histogram of the homozygous fraction $F_{ho}$ is given for a set of 175 samples (117 pregnant samples and 58 non-pregnant samples). Based on the example of FIG. 3, a value of $F_T$=0.635 is a good empirical threshold value.

The estimating may then be performed as follows:

if $F_{ho}<F_T$, the sample is determined to be pregnant;

if $F_{ho}\geq F_T$, the sample is determined to be non-pregnant.

Based on this threshold value, sample NP is classified as non-pregnant and sample P is classified as pregnant.

The value of $F_{ho}$ for a sample is not only influenced by the pregnancy state, but also by the overall level of heterozygosity of the female's DNA, which in turn depends on the ethnicity of the individual. This can be corrected for using the following approach:

determine $D_{he}$ the total number of reads on non-sex chromosomes that cover amplicons with a heterozygous allele frequency. Heterozygous amplicons may be determined by setting thresholds on $F_i$, e.g. between 0.3 and 0.7;

calculate an estimator for the heterozygosity, e.g. a heterozygous fraction $F_{he}=D_{he}/D$.

In an exemplary embodiment, the accuracy may be improved by making $F_T$ dependent on the overall level of heterozygosity of the female's DNA, estimated by $F_{he}$. This relation $F_T(F_{he})$ may be optimized using the reference data for pregnant and non-pregnant female samples.

The pregnancy estimating may then be performed as follows:

if $F_{ho}<F_T(F_{he})$, the sample is determined to be pregnant;

if $F_{ho}\geq F_T(F_{he})$, the sample is determined to be non-pregnant.

Figure 4:
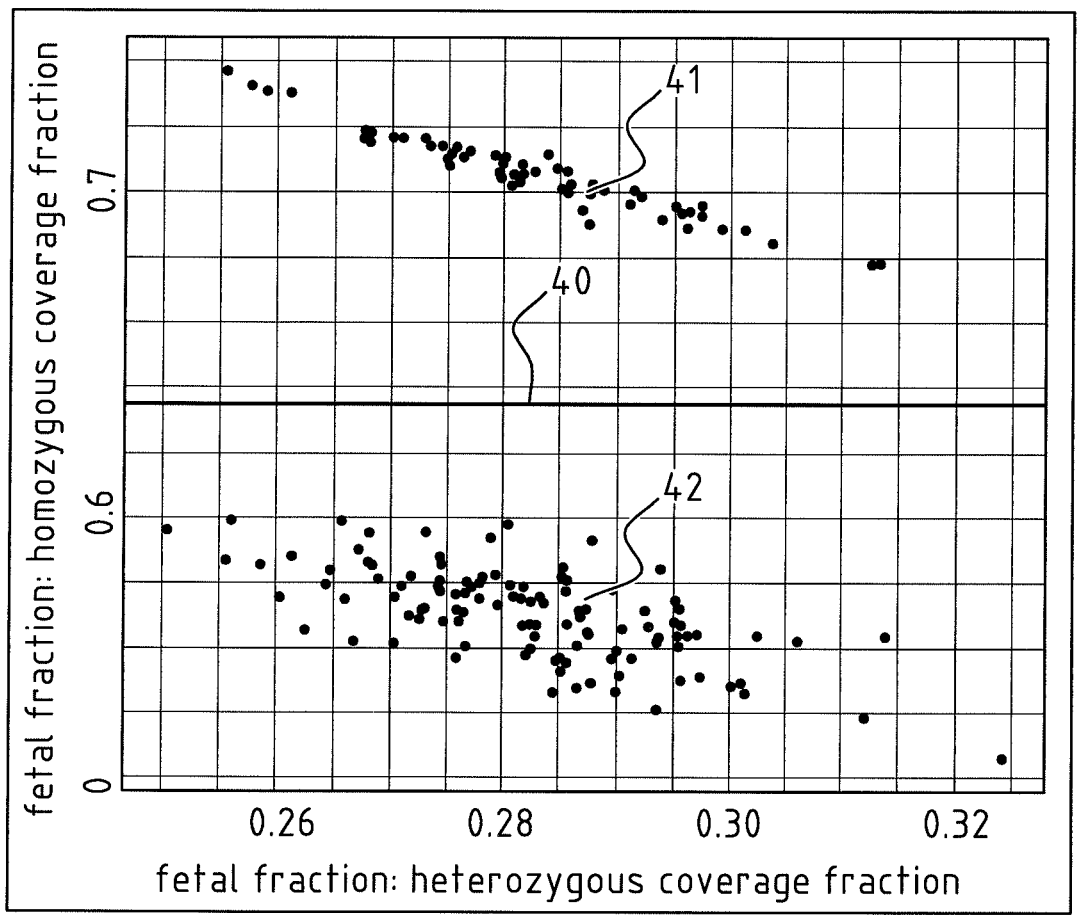
FIG. 4 is a scatterplot showing $F_{ho}$ on the y-axis and $F_{he}$ on the x-axis for a set of pregnant and non-pregnant female samples, as well as a horizontal line indicating the empirically calculated threshold value $F_T$.

The inventors have observed that the overall level of heterozygosity in the maternal DNA also influences the value of $F_{ho}$. This can be seen in FIG. 4, which shows the homozygous fraction $F_{ho}$ on the y-axis and the heterozygous fraction $F_{he}$ on the x-axis for the 175 samples. Further, in FIG. 4 it can be seen that for the 117 pregnant samples (see reference numeral 42) the homozygous fraction $F_{ho}$ is lower than $F_{Te}$=0.635 (see the horizontal line 40), and that for the 58 non-pregnant samples (see reference numeral 41) the homozygous fraction $F_{ho}$ is higher than $F_{Te}$=0.635.

Figure 5:
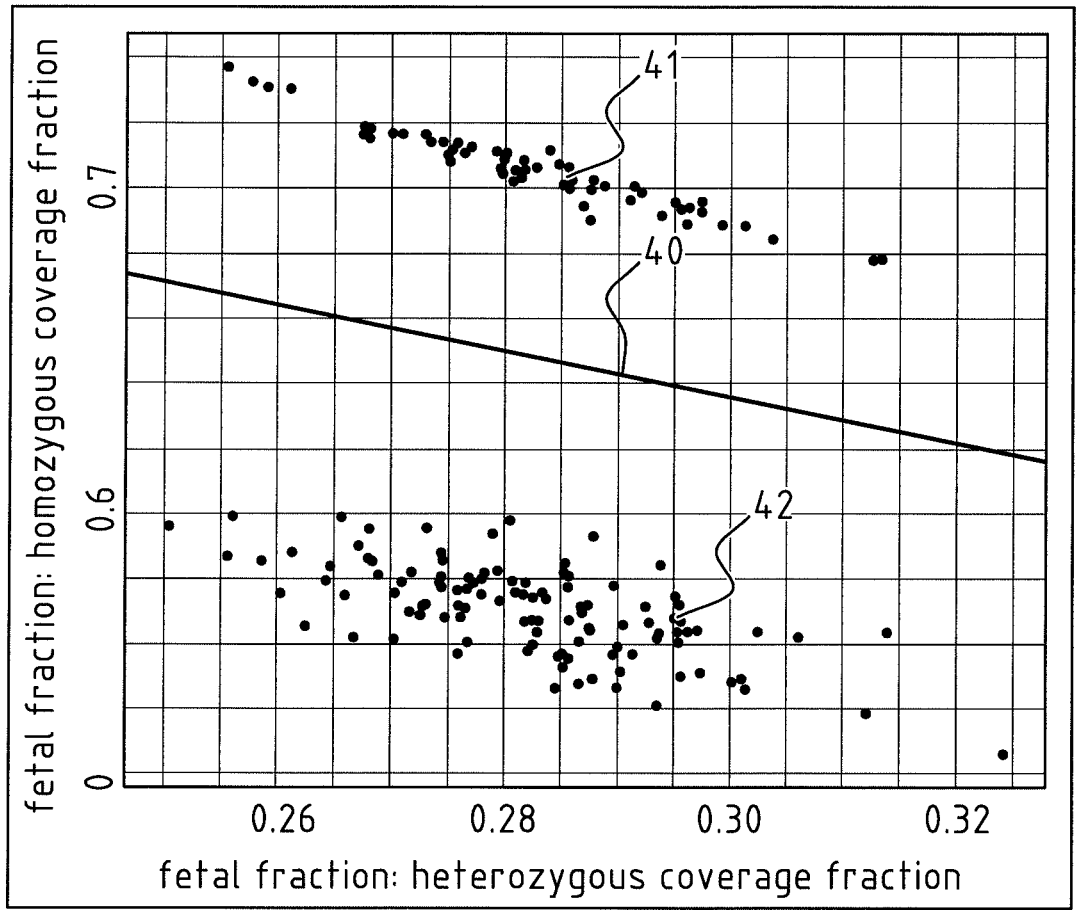
FIG. 5 is a scatterplot showing $F_{ho}$ on the y-axis and $F_{he}$ on the x-axis for a set of pregnant and non-pregnant female samples, as well as a line indicating the calculated threshold value $F_T$ ($F_{Rhe}$)

The values of the heterozygous fraction $F_{he}$ may be used to estimate a threshold value $F_T(F_{he})$, see line 40 in FIG. 5. Samples with a lower overall level of heterozygosity will tend to have a higher value $F_T(F_{he})$ and vice versa. Although a fixed threshold ($F_{Te}$=0.635) perfectly separates the groups of pregnant and non-pregnant samples, a threshold $F_T(F_{he})$ may improve the reliability of the method. Based on the data set, an empirical threshold $F_T(F_{he})$=0.86–0.75*$F_{he}$ can be established. This threshold $F_T(F_{he})$ is shown in FIG. 5, see line 40.

Figure 6:
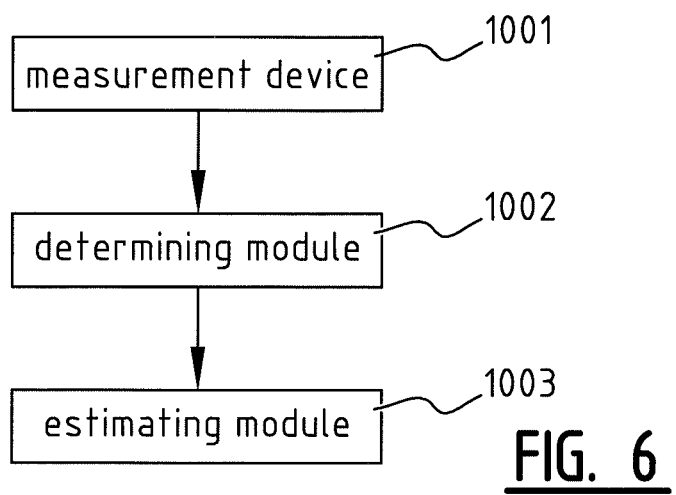
FIG. 6 is a schematic drawing of an embodiment of a system.

FIG. 6 illustrates an embodiment of a system of the invention for estimating whether or not a female is pregnant. The system comprises a measurement device 1001, a determining module 1002, and an estimating module 1003. The measurement device 1001 is configured for measuring allele presences (D) for a plurality of genetic markers of at least one chromosome, different from the X and Y chromosome, in a sample of cell-free DNA from a potentially pregnant female; each allele presence representing the presence at a genetic marker of at least one of: a reference allele of maternal or foetal origin, and an alternative allele of maternal or foetal origin. The determining module 1002 is configured for determining, based on said measured allele presences, a homozygous fraction ($F_{ho}$) thereof which is associated with purely homozygous genetic markers. The estimating module 103 is configured for estimating whether or not the female is pregnant, based on said determined fraction. The estimating may be done according to any one of the above described exemplary embodiments.

A person of skill in the art would readily recognize that steps of various above-described methods can be performed by programmed computers. Herein, some embodiments are also intended to cover program storage devices, e.g., digital data storage media, which are machine or computer readable and encode machine-executable or computer-executable programs of instructions, wherein said instructions perform some or all of the steps of said above-described methods. The program storage devices may be, e.g., digital memories, magnetic storage media such as a magnetic disks and magnetic tapes, hard drives, or optically readable digital data storage media. The embodiments are also intended to cover computers programmed to perform said steps of the above-described methods.

The functions of the various elements shown in the figures, including any functional blocks labelled as "modules", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "module" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non volatile storage. Other hardware, conventional and/or custom, may also be included.

Whilst the principles of the invention have been set out above in connection with specific embodiments, it is to be understood that this description is merely made by way of example and not as a limitation of the scope of protection which is determined by the appended claims.

The invention claimed is:

1. A method for estimating whether a female is pregnant, said method comprising:
measuring allele presences (D) for a plurality of genetic markers of at least one chromosome, different from the X and Y chromosome, in a sample of cell-free DNA from a potentially pregnant female; each allele presence representing the presence at a genetic marker of at least one of: a reference allele of maternal or fetal origin or an alternative allele of maternal or fetal origin;
determining a homozygous fraction ($F_{ho}$) thereof which is associated with purely homozygous genetic markers based on said measured allele presences;
determining a heterozygous fraction ($F_{he}$) thereof which is associated with heterozygous genetic markers based on said measured allele presences;
calculating a threshold value ($F_T$) as a function of the heterozygous fraction, wherein $F_T=0.86-0.75 \times F_{he}$; and
estimating whether the female is pregnant based on the heterozygous fraction, wherein the estimating step comprises:
estimating that the female is pregnant if the homozygous fraction is below the calculated threshold value; and
estimating that the female is not pregnant if the homozygous fraction is above the calculated threshold value.

2. The method of claim 1, wherein the determining of the homozygous fraction comprises:
calculating a corresponding number of allele frequencies for said plurality based on said measured allele presences for the plurality of genetic markers; and
determining as the homozygous fraction the fraction of said measured allele presences for which the allele frequency is 0 or 1 within a predetermined error margin.

3. The method of claim 1, wherein determining a homozygous fraction ($F_{ho}$) which is associated with purely homozygous genetic markers comprises:
calculating a corresponding number of allele frequencies for said plurality of genetic markers based on said measured allele presences for the plurality of genetic markers;
determining read counts as a function of the allele frequency for said plurality of genetic markers;
selecting a portion of the read counts; and
determining a homozygous fraction ($F_{ho}$) of said selected portion, which is associated with purely homozygous genetic markers.

4. The method of claim 1, wherein the measuring and determining steps are performed for a batch comprising a plurality of samples of the female; wherein for each sample of the batch, the homozygous fraction is calculated; and
wherein the estimating is further based on said homozygous fraction of each sample.

5. The method of claim 1, wherein the sample is maternal blood, plasma, urine, cerebrospinal fluid, serum, saliva or is transcervical lavage fluid.

6. The method of claim 1, wherein said measuring step comprises at least one of the following: polymerase chain reaction (PCR), ligase chain reaction, nucleic acid sequence based amplification (NASBA), and/or branched DNA methods.

7. The method of claim 3, comprising selecting a portion of the read counts in which the read counts with the highest and the lowest values are removed.

8. The method of claim 7, wherein the highest 5% and lowest 5% read counts are removed.

9. The method of claim 1, wherein the calculated threshold value is dependent on the overall level of heterozygosity of the female's DNA.

10. A method for estimating whether a female is pregnant, said method comprising:
measuring allele presences (D) for a plurality of genetic markers of at least one chromosome, different from the X and Y chromosome, in a sample of cell-free DNA from a potentially pregnant female; each allele presence representing the presence at a genetic marker of at least one of: a reference allele of maternal or fetal origin or an alternative allele of maternal or fetal origin;
determining a homozygous fraction ($F_{ho}$) thereof which is associated with purely homozygous genetic markers based on said measured allele presences;
determining a heterozygous fraction ($F_{he}$) thereof which is associated with heterozygous genetic markers based on said measured allele presences;
estimating whether the female is pregnant based on the heterozygous fraction, wherein the estimating step comprises:
estimating that the female is pregnant if the homozygous fraction is below a fixed threshold value; and
estimating that the female is not pregnant if the homozygous fraction is above the fixed threshold value
wherein the fixed threshold value is 0.635.

* * * * *